United States Patent
Jeong et al.

(10) Patent No.: US 8,337,614 B2
(45) Date of Patent: Dec. 25, 2012

(54) GAN SINGLE CRYSTAL SUBSTRATE AND METHOD FOR PROCESSING SURFACE OF GAN SINGLE CRYSTAL SUBSTRATE

(75) Inventors: Jin Suk Jeong, Suwon-si (KR); Ki Soo Lee, Suwon-si (KR); Kyoung Jun Kim, Suwon-si (KR); Ju Heon Lee, Suwon-si (KR); Chang Uk Jin, Suwon-si (KR)

(73) Assignee: Samsung Corning Precision Materials Co., Ltd. (KR)

( * ) Notice: Subject to any disclaimer, the term of this patent is extended or adjusted under 35 U.S.C. 154(b) by 1457 days.

(21) Appl. No.: 11/978,547

(22) Filed: Oct. 29, 2007

(65) Prior Publication Data
US 2008/0128708 A1 Jun. 5, 2008

(30) Foreign Application Priority Data

Nov. 2, 2006 (KR) .......................... 10-2006-0107664

(51) Int. Cl.
*C30B 29/38* (2006.01)
(52) U.S. Cl. ............... 117/2; 117/3; 117/89; 117/95; 117/952
(58) Field of Classification Search .................. 117/2, 3, 117/89, 95, 952
See application file for complete search history.

(56) References Cited

U.S. PATENT DOCUMENTS

| | | | |
|---|---|---|---|
| 7,889,622 B2 * | 2/2011 | Wada et al. | 369/112.28 |
| 2005/0009310 A1 | 1/2005 | Vaudo et al. | |
| 2005/0048686 A1 * | 3/2005 | Kitaoka et al. | 438/46 |
| 2005/0093101 A1 | 5/2005 | Matsumoto | |
| 2006/0273334 A1 * | 12/2006 | Nagai et al. | 257/95 |

FOREIGN PATENT DOCUMENTS

CN 1612290 A 5/2005

* cited by examiner

*Primary Examiner* — Bob M Kunemund
(74) *Attorney, Agent, or Firm* — Lerner, David, Littenberg, Krumholz & Mentlik, LLP (57) ABSTRACT

The surface of a gallium nitride single crystal substrate is processed, e.g., comprising steps by planarizing the top side and the bottom side of a gallium nitride original substrate positioned on a support bed; radiating light having wavelengths ranging from 370 to 800 nanometers (nm) onto the planarized gallium nitride original substrate; measuring transmittance of the gallium nitride original substrate; and confirming whether the transmittance is within the range of 65 to 90%. A gallium nitride single crystal substrate obtained through the method of processing the surface has high transmittance ranging from 65 to 90% measured using light having wavelengths of 370 to 800 nm. The thickness ratio ($DL_a/DL_b$) of the damage layers on the both sides of the gallium nitride single crystal substrate can be obtained within the range of 0.99 to 1.01.

11 Claims, 11 Drawing Sheets

GAN SINGLE CRYSTAL SUBSTRATE AND METHOD FOR PROCESSING SURFACE OF GAN SINGLE CRYSTAL SUBSTRATE

CROSS-REFERENCE TO RELATED APPLICATIONS

This application claims priority from Korean Patent Application No. 10-2006-0107664 filed in the Korean Intellectual Property Office on Nov. 2, 2006, the entire content of which is incorporated herein by reference.

BACKGROUND OF THE INVENTION

1. Technical Field

The present invention relates to a gallium nitride (GaN) single crystal substrate and a method of processing the surface of the same.

2. Discussion of Related Art

Generally, gallium nitride (GaN) has appropriate properties as optical devices and high-temperature and high-power devices because of a large energy band gap, a high binding force between atoms, and a high thermal conductivity. Accordingly, GaN-based semiconductor chemical compounds are variously used as materials for fabricating optical devices. Specifically, blue and green light emitting devices fabricated by using GaN are applied to a wide range of fields, such as multimedia, traffic lights, interior lights, high-density light sources, high-resolution power systems, information and communication devices, and the like.

A gallium nitride (GaN) substrate is fabricated by growing GaN on a sapphire ($Al_2O_3$) substrate which is heterogeneous. However, since gallium nitride and sapphire are different from each other in the lattice constant and the coefficient of thermal expansion, when a gallium nitride layer is formed on the sapphire substrate, a high-density crystal defect may occur. Accordingly, when the gallium nitride layer is separated from the sapphire substrate, the gallium nitride layer may become bent or cracked.

Figure 1:
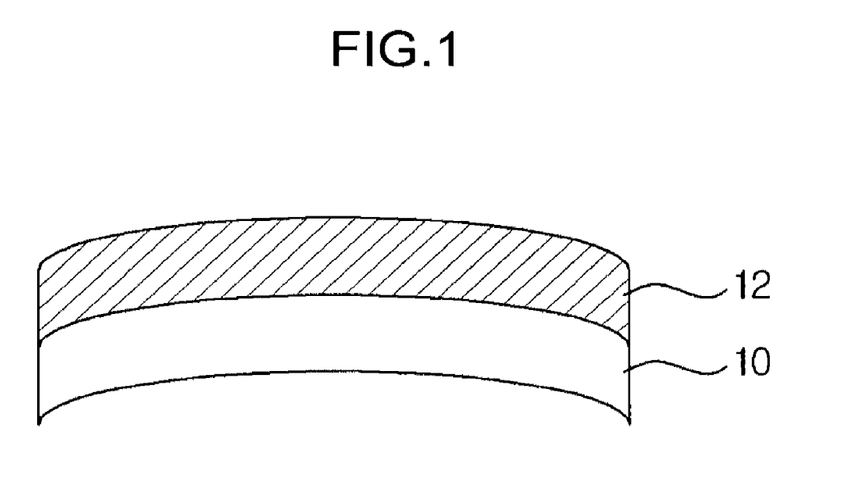
FIG. 1 is a sectional view of a heterogeneous substrate and a gallium nitride layer grown on the heterogeneous substrate.
Figure 2:
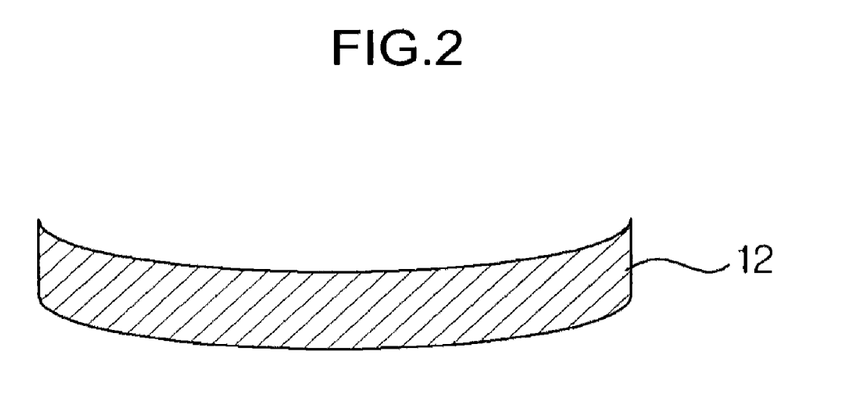
FIG. 2 is a sectional view of the gallium nitride layer separated from the heterogeneous substrate.

FIG. 1 is a sectional view of a base substrate 10 and a gallium nitride layer 12 grown on the base substrate 10, and FIG. 2 is a sectional view of the gallium nitride layer 12 separated from the base substrate.

Referring to FIGS. 1 and 2, the gallium nitride layer 12 is grown on the base substrate 10, which may be formed of sapphire, or silicon carbide, or silicon, and will be referred to as a heterogeneous substrate. However, since gallium nitride and sapphire have differences in the lattice constant and the coefficient of thermal expansion, bending may occur as illustrated in FIG. 1. Moreover, when the gallium nitride layer is separated from the heterogeneous substrate, a phenomenon, such as crystallographic tilting, occurs in the environment in that the gallium nitride layer 12 is grown as illustrated in FIG. 2. Threading dislocation occurs in high-density in the gallium nitride film, thereby affecting planarization of the surface and causing the bending.

In conventional methods to minimize the aforementioned bending, the size of a particle of an abrasive, which is used for processing the surface, is reduced by steps, so that a damaged layer of the surface is removed. Polishing equipment may be used for flattening one side or both sides of the gallium nitride substrate which is bent due to the use of the heterogeneous substrate. However, even though the surface of the gallium nitride substrate is polished by the aforementioned methods, since both sides thereof are different from each other in the extent of damage, a strain difference occurs on both sides. As a result, the substrate is bent to be concave toward the side on which the extent of damage is less. The bending of the gallium nitride layer and cracking of the gallium nitride layer due to the bending are disadvantageous to mass production yields and cost, thereby decreasing the efficiency of production.

SUMMARY OF THE INVENTION

Therefore, an aspect of the present invention provides a method of processing the surface of a gallium nitride single crystal substrate which can be easily fabricated and have high quality. A gallium nitride single crystal substrate is provided in accordance with another aspect of the invention.

A particular aspect of the present invention provides a method of processing the surface of a gallium nitride single crystal substrate, in which transmittance of the substrate is within the range of 65 to 90% when the transmittance of the substrate is measured by using light having wavelengths within the range of 370 to 800 nm after the both sides of the substrate are polished. A corresponding gallium nitride single crystal substrate having such characteristics is provided in accordance with an aspect of the invention.

A particular aspect of the invention provides a method of processing the surface of a gallium nitride single crystal substrate, in which a thickness ratio ($DL_a/DL_b$) of damage layers on both sides of a gallium nitride single crystal original substrate is within the range of 0.99 to 1.01 and transmittance thereof is within the range of 65 to 90% by polishing the both sides. A corresponding gallium nitride single crystal substrate having such characteristics is provided in accordance with an aspect of the invention.

In accordance with an exemplary embodiment, provides a gallium nitride single crystal substrate is provided which is polished on both sides thereof. Since the both sides of the substrate are polished, transmittance can be measured. When the transmittance of the substrate is measured by using light having wavelengths within the range of 370 to 800 nm the transmittance is 65 to 90%. Then, the light radiated onto the single crystal substrate uses the light formed within the range from ultraviolet rays to infrared rays.

In accordance with an exemplary embodiment, a method of processing the surface of the gallium nitride single crystal substrate is provided which comprises planarizing the top side and the bottom side of a gallium nitride original substrate positioned on a support bed; radiating light having wavelengths within the range of 370 to 800 nm onto the planarized gallium nitride substrate; measuring transmittance of the gallium nitride original substrate; and confirming whether the transmittance is 65 to 90%.

To control the transmittance of the gallium nitride single crystal substrate to be within the range of 65 to 90%, when the transmittance is out of the range of 65 to 90%, the top side or the bottom side of the gallium nitride original substrate may be additionally planarized. Then, the planarizing of the gallium nitride original substrate may further comprise: planarizing any one side of the top side and the bottom side of the gallium nitride original substrate; turning over the gallium nitride original substrate and bonding the one side being planarized to the support bed; and planarizing the other side of the top side and the bottom side of the gallium nitride original substrate.

In accordance with another exemplary embodiment, a gallium nitride single crystal substrate is provided which is polished on both sides thereof, characterized in that a thickness ratio ($DL_a/DL_b$) of damage layers on the both sides thereof is within the range of 0.99 to 1.01 and the transmittance is 65 to 90%. Then, the transmittance may be measured by using light having wavelengths within the range of 370 to 800 nm, and the light radiated onto the single crystal substrate for measuring the transmittance may be within the range from ultraviolet rays to infrared rays.

When the gallium nitride single crystal substrate which is provided by polishing the both sides by using the light having wavelengths ranging from 370 to 800 nm so that the transmittance is 65 to 90%, both of the top side and the bottom side of the substrate are evenly polished, thereby enabling to fabricate the substrate without scratches. Further, when an electrode is formed on the bottom side, an excellent electrode contact effect can be obtained.

In accordance with another exemplary embodiment, a method is provided for processing the surface of the gallium nitride single crystal substrate comprising: planarizing the top side and the bottom side of a gallium nitride original substrate positioned on a support bed; measuring a thickness ratio ($DL_a/DL_b$) of damage layers on both sides of the gallium nitride single crystal original substrate and confirming whether the thickness ratio ($DL_a/DL_b$) is within the range of 0.99 to 1.01; radiating light having wavelengths within the range of 370 to 800 nm onto the gallium nitride original substrate; measuring transmittance of the gallium nitride original substrate; and confirming whether the transmittance is within the range of 65 to 90%.

The thickness of the damage layers on the both sides of the gallium nitride single crystal original substrate may be measured by using a transmission electron microscope, and when the thickness ratio ($DL_a/DL_b$) of the damage layers being measured is out of the range of 0.99 to 1.01, the top side or the bottom side of the gallium nitride original substrate may be additionally planarized.

The planarizing of the gallium nitride original substrate may further comprise: planarizing any one side of the top side and the bottom side of the gallium nitride original substrate; turning over the gallium nitride original substrate and bonding the planarized side to the support bed; and planarizing the other side (of the top side and the bottom side) of the gallium nitride original substrate.

Generally, a compound semiconductor substrate may be fabricated, using a single crystal substrate, and it may use a homogeneous single crystal substrate of the same material as that of a compound semiconductor substrate to be grown or a heterogeneous single crystal substrate.

When the homogeneous single crystal substrate is used as a base substrate, since the base substrate and the compound semiconductor substrate to be grown, i.e., a growth layer, have no differences in the lattice constant and the coefficient of thermal expansion, a bending or crack occurring on the grown layer during the growing and separating processes can be reduced. However, when the single crystal substrate used as the base substrate and the compound semiconductor grown from the base substrate are formed of the same material, it is difficult to separate the compound semiconductor substrate from the base substrate, and it is impossible to use a laser lift-off process of dissolving an interface portion by absorbing light having different wavelengths. Moreover, when the raw material of the base substrate and the compound semiconductor is expensive, it is also difficult to include a great quantity of the base substrates.

Therefore, in a process of forming gallium nitride (GaN) which is used as the material of high-power blue light emitting diodes, the base substrate includes sapphire which is relatively inexpensive and has a different wavelength region of absorbing light from that of gallium nitride. Since heterogeneous sapphire is used as the base substrate, sapphire and gallium nitride have differences in the lattice constant and the coefficient of thermal expansion so that a gallium nitride layer may be bent and, if worse, the gallium nitride layer being grown may be damaged by a crack.

The bending of the gallium nitride layer or the crack of the gallium nitride layer which may result from the bending can be disadvantageous to yields in mass production of the gallium nitride or in the production cost thereof, so that the efficiency of production may decrease.

However, with the gallium nitride single crystal substrate and the method of processing the surface of the same according to embodiments of the present invention, it is possible to fabricate a gallium nitride single crystal substrate which has a transmittance within the range of 65 to 90%, or which has a thickness ratio ($DL_a/DL_b$) of the damage layers on both sides of the gallium nitride single crystal substrate within a range of 0.99 to 1.01 and has the transmittance within the range of 65 to 90%. Accordingly, since the gallium nitride layer is prevented from being bent, the mass production yields and cost of the gallium nitride substrate can be very favorable.

BRIEF DESCRIPTION OF THE DRAWINGS

The above and other features and advantages of embodiments of the present invention will be apparent from the detailed description of the preferred embodiments thereof with reference to the attached drawings in which.

DETAILED DESCRIPTION OF THE INVENTION

Embodiments of the present invention will now be described more fully hereinafter with reference to the accompanying drawings, in which preferred embodiments of the invention are shown. This invention may, however, be embodied in different forms and should not be construed as limited to the embodiments set forth herein.

First Exemplary Embodiment

Figure 3:
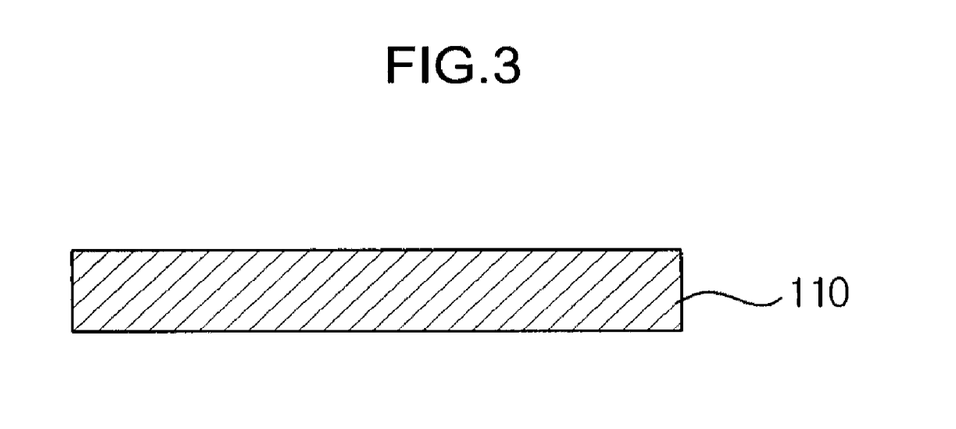
FIG. 3 is a sectional view of a gallium nitride single crystal substrate according to a first exemplary embodiment of the present invention.

FIG. 3 is a sectional view of a gallium nitride single crystal substrate 110 according to a first exemplary embodiment of the present invention. Both sides of the gallium nitride single crystal substrate 110 are polished and have uniform surface roughness. As a result of measuring transmittance of the gallium nitride single crystal substrate 110 by using light (ultraviolet rays, visible rays, or infrared rays) having wavelengths within the range of 370 to 800 nm, the transmittance thereof is within the range of 65 to 90%.

Figure 4:
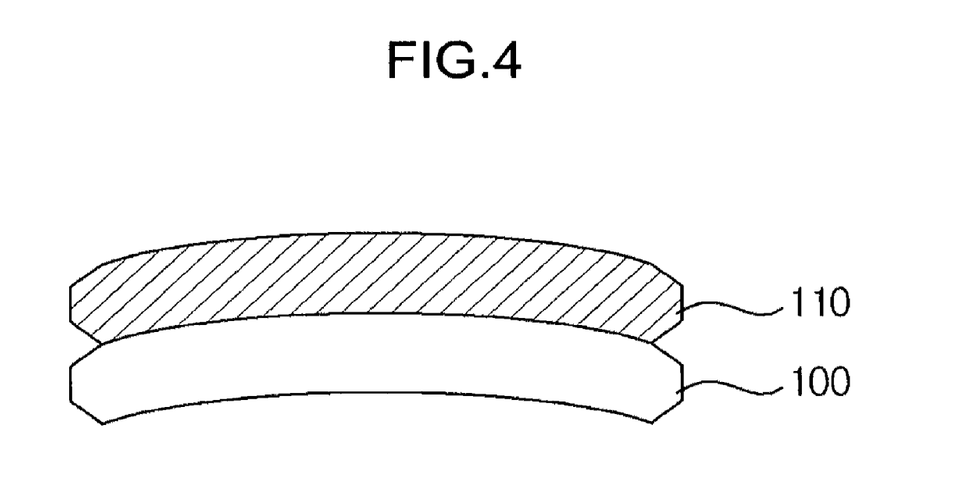
FIG. 4 is a sectional view of the gallium nitride single crystal substrate grown on a base substrate.
Figure 5:
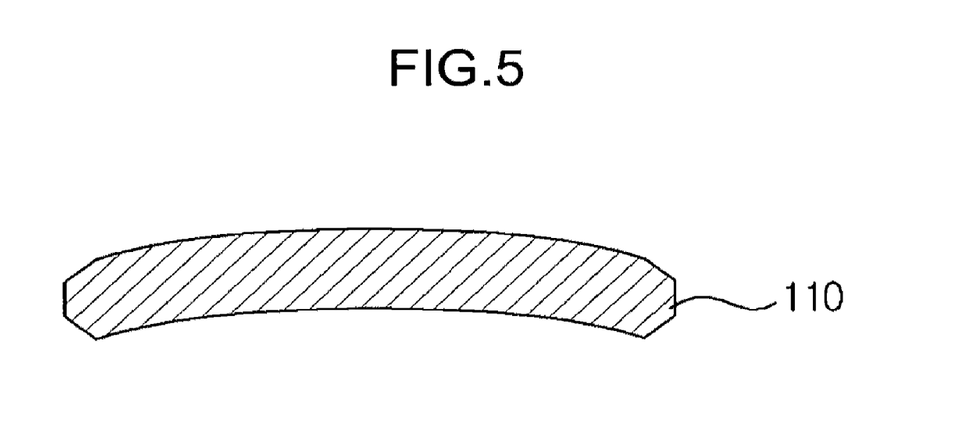
FIG. 5 is a sectional view of the gallium nitride single crystal substrate separated from the base substrate.

FIG. 4 is a sectional view of the gallium nitride single crystal substrate 110 grown on a base substrate 100, and FIG. 5 is a sectional view of the gallium nitride single crystal substrate 110 separated from the base substrate 100.

As illustrated in FIG. 4, the gallium nitride single crystal substrate 110 is grown on the base substrate 100. Sapphire, silicon carbide (SiC) or gallium arsenide (GaAs) may be used as the base substrate 100 and sapphire is used in this exemplary embodiment.

Next, as illustrated in FIG. 5, the gallium nitride single crystal substrate 110 formed on the base substrate 100 is separated from the base substrate 100. A laser lift-off process for partially dissolving the interface between the base substrate and the gallium nitride substrate may be performed by absorbing light of a different wavelength range using the sapphire substrate. The laser lift-off method may be applied as a method for separating the gallium nitride single crystal substrate 110 from the base substrate 100.

Specifically, after a gallium nitride layer is grown on the sapphire substrate which is the base substrate 100, laser light is radiated on the transparent sapphire substrate to dissolve a part of the gallium nitride layer around the interface between the gallium nitride layer and the sapphire substrate, thereby separating the grown gallium nitride layer from the sapphire substrate. As shown in FIG. 5, the gallium nitride single crystal substrate 110 separated from the base substrate remains bent due to the differences of the lattice constant and the coefficient of thermal expansion from those of the base substrate.

Figure 10:
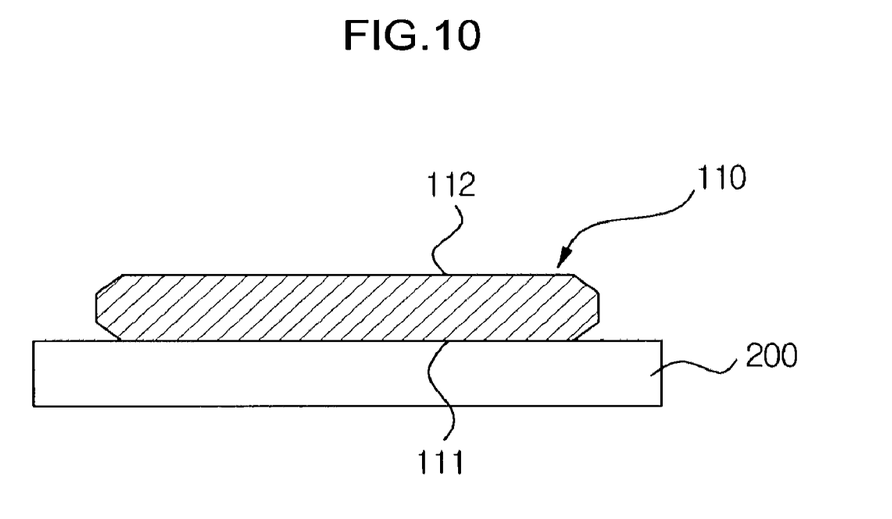
Figure 11:
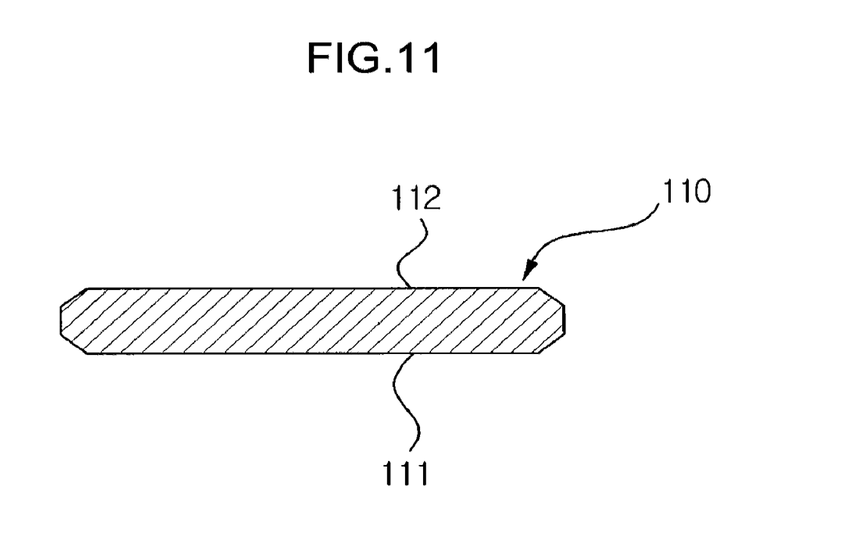
Figure 12:
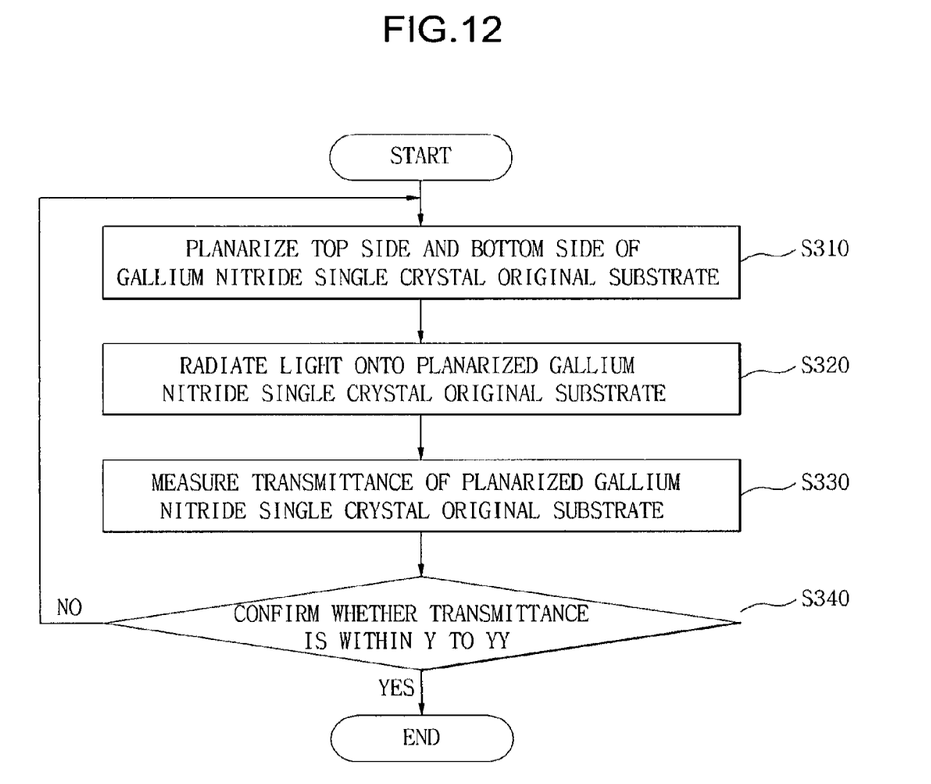
FIG. 12 is a flow chart for explaining a method of processing the surface of the gallium nitride single crystal substrate according to the first exemplary embodiment of the present invention.

A method of processing the surface for planarization of the gallium nitride single crystal substrate according to an embodiment of the present invention will be described below:

FIGS. 6 through 11 are sectional views illustrating a method of processing the surface of a gallium nitride single crystal substrate 110 according to an embodiment of the present invention, and FIG. 12 is a flow chart for explaining a method of processing the surface of the gallium nitride single crystal substrate according to a first exemplary embodiment of the present invention.

Figure 6:
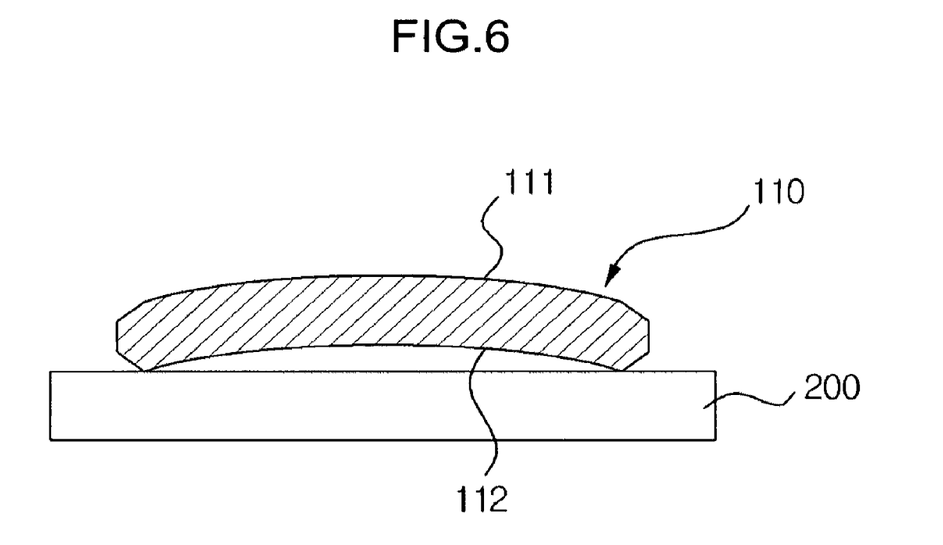
FIGS. 6 through 11 are sectional views of a method of processing the surface of the gallium nitride single crystal substrate according to an embodiment of the present invention.

As illustrated in FIG. 6, the gallium nitride single crystal substrate 110 is positioned on a support bed 200 for a surface process. Metal materials or an aluminum or glass substrate may be used as materials of the support bed 200. The top side and the bottom side of the gallium nitride single crystal substrate 110 are indicated as a first side (N-face) 111 and as a second side (Ga-face) 112, and the second side 112 is bonded to the support bed 200, using wax.

Figure 7:
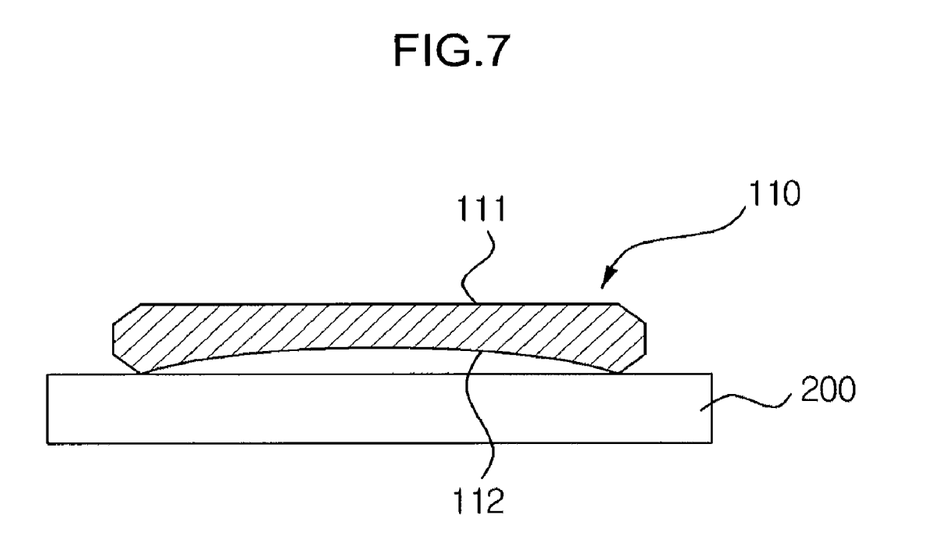

As illustrated in FIG. 7, when the second side 112 of the gallium nitride single crystal substrate 110 is bonded to the support bed 200, the first side 111 is planarized. As a device for planarization, a mechanical device using a diamond wheel, a diamond surface plate, or an abrasive surface plate using slurry may be used. A light device is used to maintain the bending state of the gallium nitride single crystal substrate 110, so that the bending portion of the first side 111 is polished to be planarized without changing the gallium nitride single crystal substrate 110.

Subsequently, it is determined whether the extent of flatness and the damage layer of the surface are within predetermined standards, by radiating laser light onto the surface of the first side 111. When the surface roughness is not within the standard, the bending portion of the first side 111 may be again polished.

Figure 8:
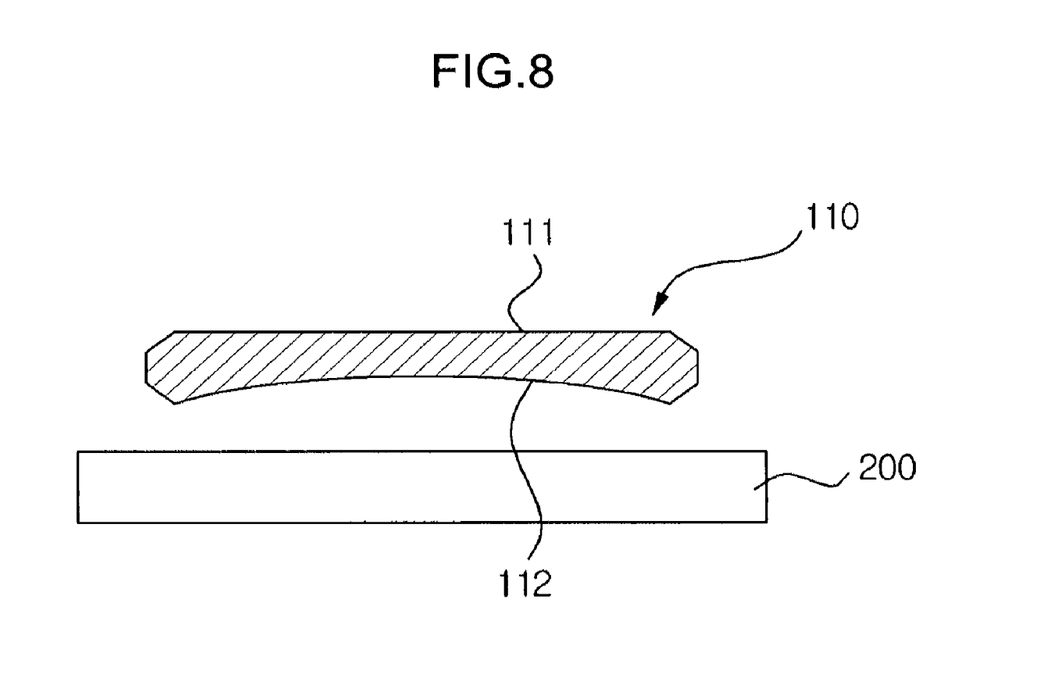
Figure 9:
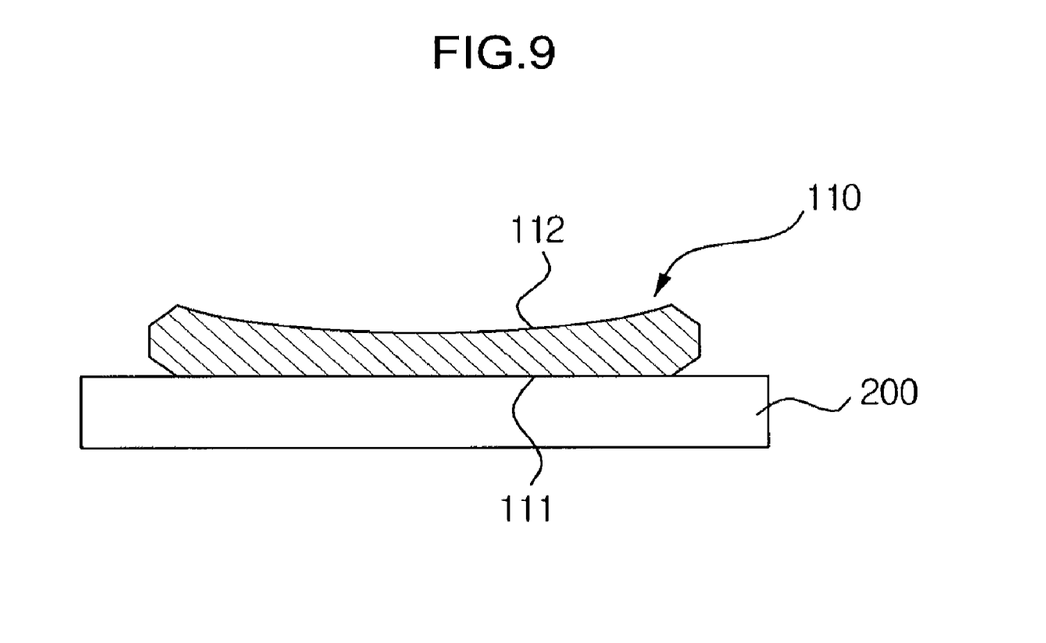

When the surface roughness of the first side 111 satisfies the standard specification, as illustrated in FIGS. 8 and 9, the gallium nitride single crystal substrate 110 is separated from the support bed 200 and the planarized first side 111 is bonded to the surface of the support bed 200 by the wax and is positioned so that the second side 112 of the gallium nitride single crystal substrate 110 faces upward.

Subsequently, as illustrated in FIG. 10, when the first side 111 of the gallium nitride single crystal substrate 110 is bonded to the surface of the support bed 200, the second side 112 is planarized. The second side 112 may be planarized, using the same device for planarization used for planarizing the first side 111. In this case, a light device is used to maintain the bending state of the gallium nitride single crystal substrate 110, so that the bending portion of the second side 112 is polished to be planarized without changing the gallium nitride single crystal substrate 110.

After the planarization, it is determined whether the extent of flatness and the damage layer of the surface are within predetermined standards, by radiating laser light onto the surface of the second side 112. When the surface roughness is not within the standard, the bending portion of the second side 112 again undergoes the polishing process.

Subsequently, the gallium nitride single crystal substrate 110, the second side 112 of which is completely planarized is separated from the support bed 200, thereby completing the gallium nitride single crystal substrate 110 as illustrated in FIG. 11.

FIG. 12 is a flow chart for explaining a method of processing the surface of the gallium nitride single crystal substrate according to a first exemplary embodiment of the present invention.

The method of processing the surface of the gallium nitride single crystal substrate comprises steps of: planarizing the top side and the bottom side of the gallium nitride original substrate positioned on the support bed at S310; radiating light having wavelengths within the range of 370 to 800 nm onto the planarized gallium nitride original substrate at S320; measuring transmittance of the gallium nitride original substrate at S330; and confirming whether the transmittance is within the range of 65 to 90% at S340.

The description with reference to FIGS. 4 through 11 may be referred to for the step of planarizing the top side and the bottom side of the gallium nitride original substrate positioned on the support bed at S310.

To control the transmittance of the gallium nitride single crystal substrate to be within the range of 65 to 90%, the top side or the bottom side of the gallium nitride original substrate may be additionally planarized when the transmittance is out of the range of 65 to 90%. Then, the planarization step at S310 may further comprise steps of: planarizing any one side of the top side and the bottom side of the gallium nitride original substrate, turning over the original substrate and bonding the one side being planarized to the support bed, and planarizing the other side of the gallium nitride original substrate.

In accordance with an embodiment of the present invention, both sides of the gallium nitride single crystal substrate are polished by using the light within the range of 370 to 800 nanometers (nm) so that the transmittance becomes within the range of 65 to 90%. As a result, the top side and the bottom side have the uniform surface roughness without any defects and when an electrode is formed on the surface of the substrate, the electrode contact is excellent.

Second Exemplary Embodiment

Figure 13:
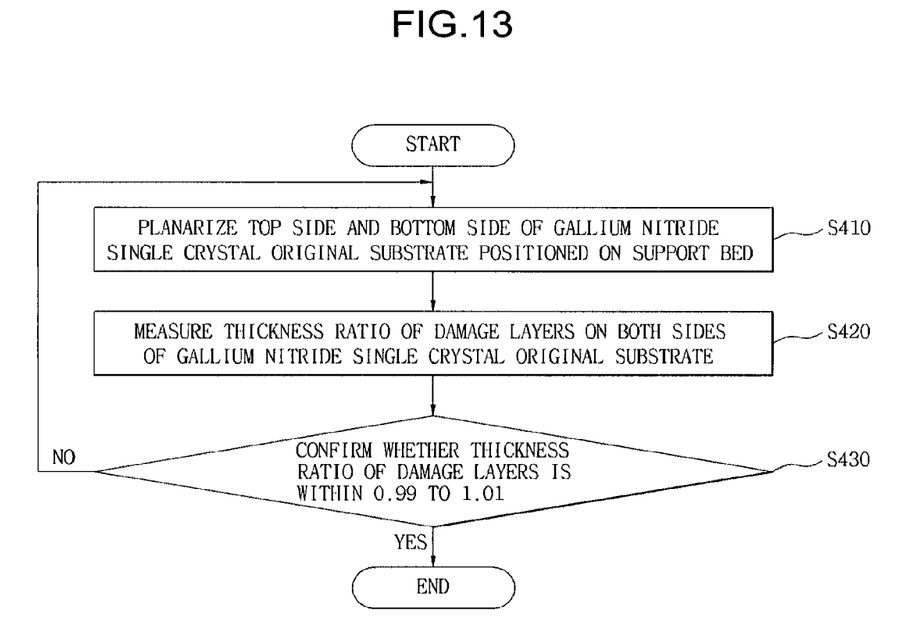
FIG. 13 is a flow chart for explaining a method of processing the surface of the gallium nitride single crystal substrate according to a second exemplary embodiment of the present invention.

FIG. 13 illustrates a flow chart for explaining a method of processing the surface of a gallium nitride single crystal substrate according to a second exemplary embodiment of the present invention.

The gallium nitride single crystal substrate according to the second exemplary embodiment and the method of processing the surface of the same are similar to the gallium nitride single crystal substrate 110 according to the first exemplary embodiment and the method of processing the surface of the same as described above. However, in the second exemplary embodiment, the method of processing the surface of the gallium nitride single crystal substrate comprises a step of measuring a thickness ratio ($DL_a/DL_b$) of damage layers on both sides of the gallium nitride single crystal original substrate, instead of the step of measuring the transmittance of the gallium nitride single crystal substrate in the first exemplary embodiment.

In the first exemplary embodiment, after planarizing the gallium nitride single crystal substrate, the method of processing the surface thereof comprises the steps of radiating the light having wavelengths within the range of 370 to 800 nanometers (nm) onto the planarized gallium nitride original substrate, measuring transmittance of the gallium nitride original substrate, and confirming whether the transmittance is within the range of 65 to 90%. However, in the second exemplary embodiment of the present invention, after planarizing the gallium nitride single crystal substrate, the method of processing the surface thereof comprises steps of: measuring a thickness ratio ($DL_a/DL_b$) of damage layers on both sides of the gallium nitride single crystal original substrate, and confirming whether the thickness ratio ($DL_a/DL_b$) of the damage layers is within the range of 0.99 to 1.01.

The thickness of the damage layers on the both sides of the gallium nitride single crystal original substrate may be measured by using a transmission electron microscope and the like. When the thickness ratio ($DL_a/DL_b$) of the damage layers is out of the range of 0.99 to 1.01, the top side or the bottom side of the gallium nitride original substrate may be additionally planarized.

When a desired thickness ratio ($DL_a/DL_b$) of the damage layers is obtained, the method may further comprise steps of: radiating light having wavelengths within the range of 370 to 800 nm onto the gallium nitride original substrate; measuring transmittance of the gallium nitride original substrate; and confirming whether the transmittance is within the range of 65 to 90%.

Figure 14:
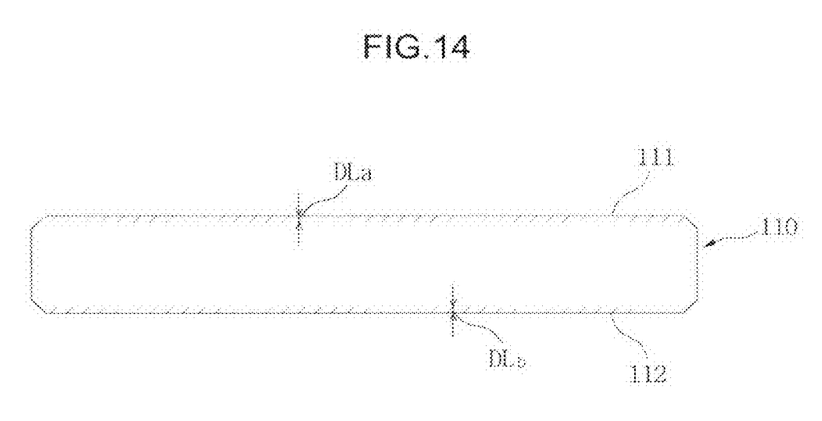
FIG. 14 is a sectional view for explaining a thickness of a damage layer of the gallium nitride single crystal substrate according to the second exemplary embodiment of the present invention.

FIG. 14 is a sectional view for explaining a thickness of a damage layer of the gallium nitride single crystal substrate according to the second exemplary embodiment of the present invention.

As illustrated in FIG. 14, the thickness of a damage layer on the top side of the gallium nitride single crystal substrate, that is, a first side 111, is $DL_a$ and the thickness of a damage layer on the bottom side, that is, a second side 112, is $DL_b$. Accordingly, the thickness ratio ($DL_a/DL_b$) of the damage layers may indicate the thickness ratio of the damage layers occurred on the both sides of the gallium nitride single crystal substrate during the planarization process.

Figure 15A:
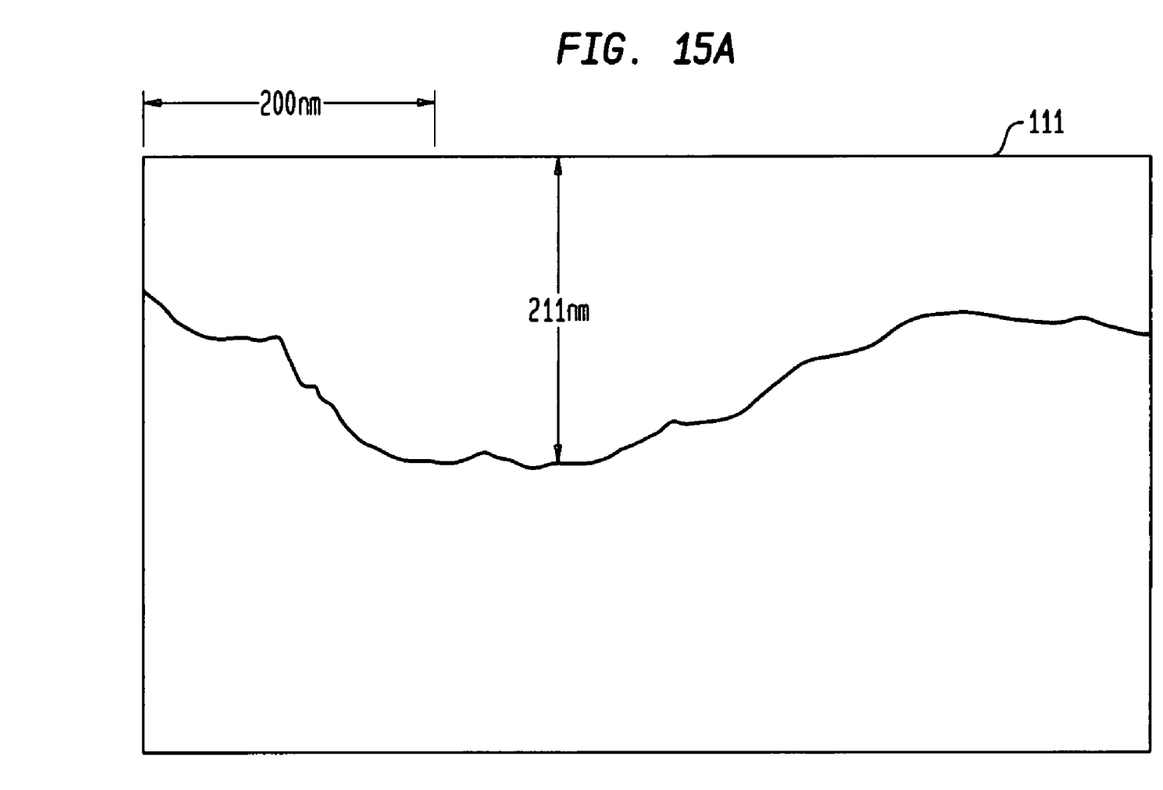
FIGS. 15A and 15B are pictures of the damage layers on the top side and the bottom side of the gallium nitride single crystal substrate.
Figure 15B:
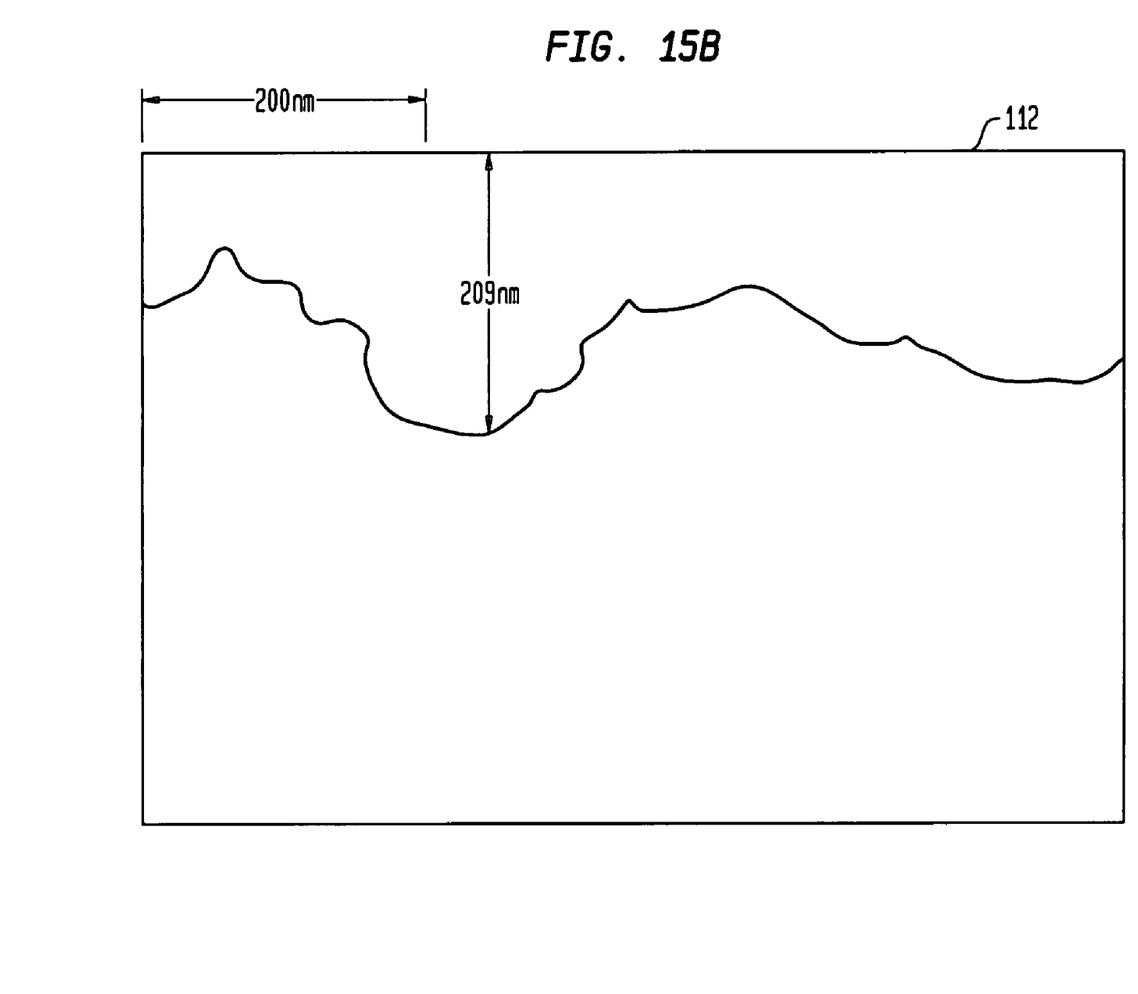

When the thickness ratio of the damage layers on both sides of the gallium nitride single crystal substrate approximates 1, the bending of the substrate can be minimized. FIGS. 15A and 15B respectively show the first side (N-face) 111 and the second side 112 (Ga-face) of the gallium nitride single crystal substrate before the damage layers are removed after the both sides are polished. Referring to FIGS. 15A and 15B, the thickness of the damage layer on the first side is 211 nm and the thickness of the damage layer on the second side is 209 nm. Since the thickness ratio of the damage layers on the both sides is 1.01, which approximates 1, it is considered as being in a very good condition. The damage layers can be removed through the additional processes, such as a reactive ion etching process, after the both sides of the gallium nitride substrate are polished.

Figure 16:
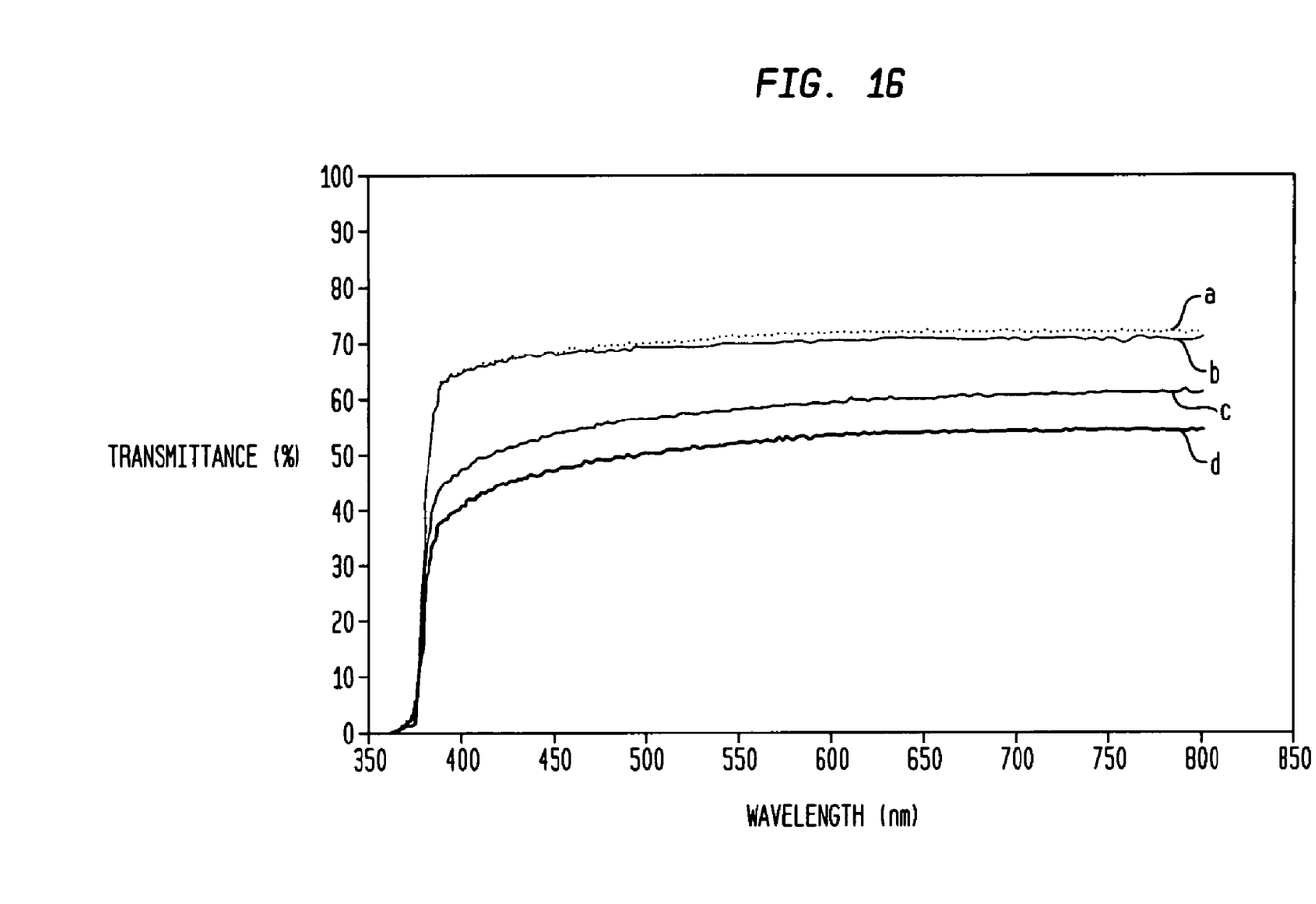
FIG. 16 is a graph illustrating the result of measuring the transmittance of the gallium nitride single crystal substrate being polished.

The results of measuring the transmittance of the gallium nitride single crystal substrate according to an embodiment of the present invention are shown in Table 1 and FIG. 16.

In the substrates a and b with both sides being polished, the transmittance rapidly increases from the wavelength range of 370 nm and the high transmittance above 65% is indicated in most of the wavelength range. However, in the substrates c and d with one side being polished, the low transmittance below 65% is indicated in the entire wavelength range.

TABLE 1

| Wavelength (nm) | BASE | Both Side Polished GaN Wafer #1 | Both Side Polished GaN Wafer #2 | Single Side Polished GaN Wafer #1 | Single Side Polished GaN Wafer #2 |
|---|---|---|---|---|---|
| 800 | 99.68 | 72.2 | 71 | 54.79 | 61.79 |
| 750 | 100.45 | 72.34 | 71.24 | 54.68 | 61.59 |
| 700 | 100.21 | 72.6 | 71.01 | 54.42 | 60.85 |
| 650 | 100.46 | 72.4 | 70.68 | 54.31 | 60.44 |
| 600 | 100.16 | 71.75 | 70.72 | 53.34 | 59.64 |
| 550 | 100.21 | 71.3 | 70.05 | 52.26 | 58.32 |
| 500 | 100.25 | 70.48 | 69.2 | 50.32 | 56.54 |
| 450 | 99.63 | 68.42 | 68.04 | 47.18 | 53.92 |
| 400 | 100.59 | 65.64 | 65.77 | 41.05 | 47.49 |
| 380 | 100.27 | 43.7 | 43.34 | 24.22 | 30.92 |
| 370 | 100.31 | 0.2 | 0.4 | 1.02 | 1.84 |

After the both sides of the gallium nitride single crystal substrate are polished, the transmittance and the thickness ratio of the damage layers are measured to confirm whether the gallium nitride single crystal substrate has no defect and has excellent quality.

In the gallium nitride single crystal substrate produced by the method of processing the surface thereof in accordance with an embodiment of the present invention, when the transmittance of the substrate is measured by using the light having wavelengths within the range of 370 to 800 nm, the transmittance is within the range of 65 to 90%.

In the gallium nitride single crystal substrate produced by the method of processing the surface thereof in accordance with an embodiment of the present invention, the thickness ratio ($DL_a/DL_b$) of the damage layers on the both sides is within the range of 0.99 to 1.01 and the transmittance is within the range of 65 to 90%.

In the gallium nitride single crystal substrate produced by the method of processing the surface thereof in accordance with an embodiment of the present invention, since bending does not occur, it is advantageous to mass production yields and the production cost, so that production efficiency is significantly improved.

When the gallium nitride single crystal substrate is used which is produced by the method of processing the surface thereof in which the transmittance is high and the thickness ratio of the damage layers is proximate to 1, high production yield and performance are obtained in various application fields. Furthermore, since the top side and the bottom side of the substrate are uniformly polished, when the electrode is formed on the surface of the substrate, excellent electrode contact effects are obtained.

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents. The scope of the claims, therefore, should be accorded the broadest interpretation so as to encompass all such modifications and similar arrangements.

The invention claimed is:

1. A substrate comprising:
a gallium nitride single crystal substrate which is provided by polishing both sides of the single crystal substrate, wherein when transmittance of the single crystal substrate is measured by using light having wavelengths within the range of 370 to 800 nanometers (nm), the transmittance is within the range of 65 to 90%.

2. A method of processing the surface of a gallium nitride single crystal original substrate, comprising steps of:
planarizing the top side and the bottom side of a gallium nitride original substrate positioned on a support bed;
radiating light having wavelengths within the range of 370 to 800 nm onto the planarized gallium nitride original substrate;
measuring transmittance of the gallium nitride original substrate; and
confirming whether the transmittance is within the range of 65 to 90%.

3. The method according to claim 2, further comprising:
when the transmittance measured in the measuring step is not within the range of 65 to 90%, additionally planarizing at least one of the top side or the bottom side of the gallium nitride original substrate.

4. The method according to claim 2, wherein the planarizing step further comprises steps of:
planarizing any one of the top side or the bottom side of the gallium nitride original substrate,
turning over the original substrate and bonding the planarized one side to the support bed, and
planarizing the other one of the top side or the bottom side of the gallium nitride original substrate.

5. A substrate, comprising:
a gallium nitride single crystal substrate which is provided by polishing both sides of the single crystal substrate, wherein a thickness ratio ($DL_a/DL_b$) of damage layers on both sides of the gallium nitride single crystal original substrate is within the range of 0.99 to 1.01 and transmittance is within the range of 65 to 90%.

6. The substrate according to claim 5, wherein the transmittance is measured by using light having wavelengths within the range of 370 to 800 nanometers (nm).

7. The substrate according to claim 5, wherein the light to be radiated on the gallium nitride single crystal substrate for measuring the transmittance is from ultraviolet rays to infrared rays.

8. A method of processing the surface of a gallium nitride single crystal substrate, comprising steps of:
planarizing the top side and the bottom side of a gallium nitride original substrate positioned on a support bed;
measuring a thickness ratio ($DL_a/DL_b$) of damage layers on the top and bottom sides of the gallium nitride original substrate;
confirming whether the thickness ratio ($DL_a/DL_b$) of the damage layers is within the range of 0.99 to 1.01;
radiating light having wavelengths within the range of 370 to 800 nm onto the gallium nitride original substrate;
measuring transmittance of the gallium nitride original substrate; and
confirming whether the transmittance is within the range of 65 to 90%.

9. The method according to claim 8, wherein the thicknesses of the damage layers on the top and bottom sides of the gallium nitride original substrate are measured by using a transmission electron microscope.

10. The method according to claim 8, wherein when the thickness ratio ($DL_a/DL_b$) of the damage layers is out of the range of 0.99 to 1.01, additionally planarizing at least one of the top side or the bottom side of the gallium nitride original substrate.

11. The method according to claim 8, wherein the planarizing step further comprises steps of:
planarizing any one of the top side or the bottom side of the gallium nitride original substrate,
turning over the gallium nitride original substrate and bonding the planarized one side to the support bed, and
planarizing the other of the top or bottom sides of the gallium nitride original substrate.

* * * * *